United States Patent [19]

Teurlings

[11] Patent Number: 4,881,533
[45] Date of Patent: Nov. 21, 1989

[54] VARIANCE WRIST BRACE

[76] Inventor: Luc Teurlings, 711 Wilcox Ave., #304, Los Angeles, Calif. 90038

[21] Appl. No.: 163,869

[22] Filed: Mar. 3, 1988

[51] Int. Cl.$^4$ .................. A61F 5/04; A61F 13/00; A41D 13/08; A63D 5/00
[52] U.S. Cl. .................. 128/87 R; 128/878; 2/16; 273/54 B
[58] Field of Search .................. 128/87 R, 77, 89 R, 128/87 A, 155, 156; 2/16, 20, 161 A; 273/54 B

[56] References Cited

U.S. PATENT DOCUMENTS

| | | | |
|---|---|---|---|
| 2,077,202 | 4/1937 | Barrie | 273/54 B |
| 3,496,573 | 2/1970 | Kuchar et al. | 273/54 B |
| 3,512,776 | 5/1970 | Thomas, Sr. | 273/54 B |
| 3,598,408 | 8/1971 | Klose | 273/54 B |
| 3,606,614 | 9/1971 | Dimitroff | 273/54 B |
| 4,051,553 | 10/1977 | Howard | 2/161 A |
| 4,071,913 | 2/1978 | Rector | 2/161 A |
| 4,198,709 | 4/1980 | Clayton | 273/54 B |
| 4,374,439 | 2/1983 | Norman | 273/54 B |
| 4,624,016 | 11/1986 | Luevano | 2/161 A |

Primary Examiner—Robert A. Hafer
Assistant Examiner—Michael Brown

[57] ABSTRACT

A versatile orthopedic wrist brace to support the wrist joint in excessive weight bearing activities such as gymnastics. The wrist brace includes an adjustable, removable palmar base support, that is a palmar pad 4 which elevates the wrist in a support position reducing the extension angle at the wrist joint, thus relieving pressure and pain in the wrist. This palmar pad 4 is designated specifically to compensate for imbalanced load forces which are the result of ulnar variance in support position at the wrist joint. The wrist brace is also made of a dorsal base support pad 1 including an elongated reinforcing member that consists of a rigid material and a malleable material for comfort. This dorsal reinforcing member 1 supports the wrist and the upper part of the hand in extension and might have two malleable side support members 8, 9. A wrist strap 5 extends from the dorsal base support 1, adheres to the palmar base support 4 and is wrapped around the user's wrist to hold both base supports into place. Two straps 10, 12 extend from both top sides of the palmar base support 4 to adhere its free ends to the dorsal base support 1 on the back side of the hand. One of these straps 10 contours the thumb and the shorter strap 12 contours the little finger side of the hand.

8 Claims, 11 Drawing Sheets

VARIANCE WRIST BRACE

BACKGROUND—FIELD OF INVENTION

This invention relates to wrist braces, especially to wrist supports designed for gymnasts, to relieve wrist pain or to reduce load forces in the wrist joint even when no pain is present, in order to increase the functional and intensity level of the gymnasts training. This orthopedic wrist brace compensates for ulnar variance and extension to reduce load forces in the wrist joint in weight bearing activities.

BACKGROUND—DESCRIPTION OF PRIOR ART

Heretofore, wrist braces have been designed to support and to prevent various motions at the wrist joint. Many wrist supports have been made specifically for bowlers, such as the following U.S. Pat. Nos.;
 Anderson 3,117,786; Thomas 3,512,776; Klose 3,598,408; Andolino 3,728,738; Benoun, et. al. 3,779,550; Hashimoto 3,815,908; Ensinger 3,829,090; and Hollman 3,871,029.

Other prior art wrist braces offer limited mobility for injured wrists or provide general stability of the wrist in athletes, such as the following U.S. Pat. Nos.;
 Risher and Martin 2,794,638; Stubbs 3,238,939; Gamm 3,327,703; Hawkins 3,970,305; Norman 4,047,250; Massman 4,088,318; Knowles Jr. 4,183,098; DeMarco 4,309,991; and Nelson 4,584,993.

No prior art wrist braces however, take into consideration ulnar variance and its transfer load forces at the wrist joint in an extended support position.

This invention is developed to solve many wrist problems that gymnasts have in their weight bearing activities. In interaction with the UCLA Orthopedic Sports Medicine Group, I am currently involved in a research project examining the cause of wrist pain, specifically in gymnasts. Our study is the first one that has ever looked at the ulnar variance (explained later), as it appears in the gymnast's wrist joint. Our results have shown that positive ulnar variance is dominant in competitive gymnasts, and that this positive variance is the cause for most of the gymast's wrist pain. Since our study is unique in the orthopedic sports medicine field, and since our results have only recently been revealed, it is very unlikely that any wrist orthotic has been developed to compensate for ulnar variance. This wrist brace is designed to allow flexion (in which no pain is reported) but to restrict movements within the wrist joint which are the result of positive or negative ulnar variance, in an extended support position.

Some prior art wrist braces for athletes, use a dorsal pad on the back of the hand, to prevent extension. The majority of these braces encase the hand similar to a glove, therefore are regarded by many users as too bulky and restrictive in motions that do not cause pain. The pads used are either too thin and consequently wear out too fast resulting in a substantial loss of support. Others are too stiff resulting in a significantly limited range of motion.

Additionally, none of these prior art wrist braces feature a palmar pad in the palm of the hand, which allows compensation of load forces in a positive (or negative) ulnar variant wrist in a support position. Even though some prior art wrist braces are designed to support the wrist in an extended position, none of them are specifically designed to reduce this extension angle.

OBJECTS AND ADVANTAGES

Accordingly, I claim the following as objects and advantages of this invention;
 to provide a wrist brace that uses a pad on the palmar side of the hand (right above the distal and proximal carpal row) in order to:
 transfer load forces more equally in a positive (or negative) ulnar variant wrist in a support position by "cushioning" higher or lower on the radial (thumb) side than on the ulnar (little finger) side according to the ulnar variance (see FIG. 8).
 post (or lift up) the proximal palmar side of the hand such that the extension angle is reduced in a support position (see FIG. 10)
 "Cushion" wrist (carpal bones) and protect them from impact loads (such as in back hand springs, dive rolls, hand stands, walk overs etc.).
 to provide a wrist brace that is less restrictive in the range of motion where it is not needed in support, and
 to provide a stronger, more durable, and more comfortable dorsal pad to restrict extension in a support position more efficiently.

Figure 8:
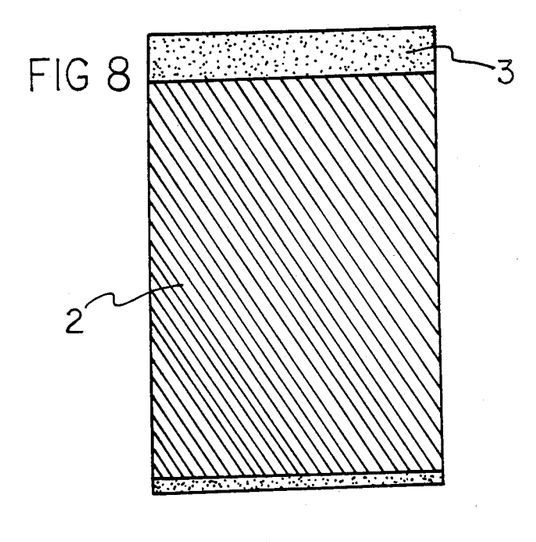
FIG. 8 shows the top of the dorsal pad.
Figure 9:
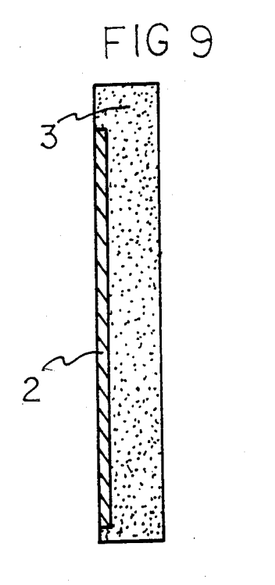
FIG. 9 shows the side of the dorsal pad.

In the study I am engaged in with the UCLA Orthopedic Sports Medicine Group, it is shown that many gymnasts have what is called "positive ulnar variance". Positive ulnar variance is indicated by a longer ulna relative to the radius, resulting in imbalanced forces at the wrist joint. This positive ulnar variance causes damage to the triangular fibrocartilage complex which is a cushion between the ulna and carpals (the lunate and the triquetrum). In order to correct for this imbalance in load forces between ulna and radius, this invention introduces the palmar variance pad which is thicker on the radial side than on the ulnar side in case of positive ulnar variance. This palmar pad is designed to more evenly distribute axial loads through the forearm in a weight bearing support of a positive ulnar variance wrist, such that less damage is caused to the triangular fibrocatilage. Positive variance is illustrated in FIG. 9 (III), and FIG. 8 indicates the ability of the palmar variance pad to compensate for positive variance.

Since the results of our study are unique, no prior art wrist brace has been developed to correct this problem, and/or to prevent further bone deformation of the wrist joint in a gymnast.

Figures 5, 6, 7:
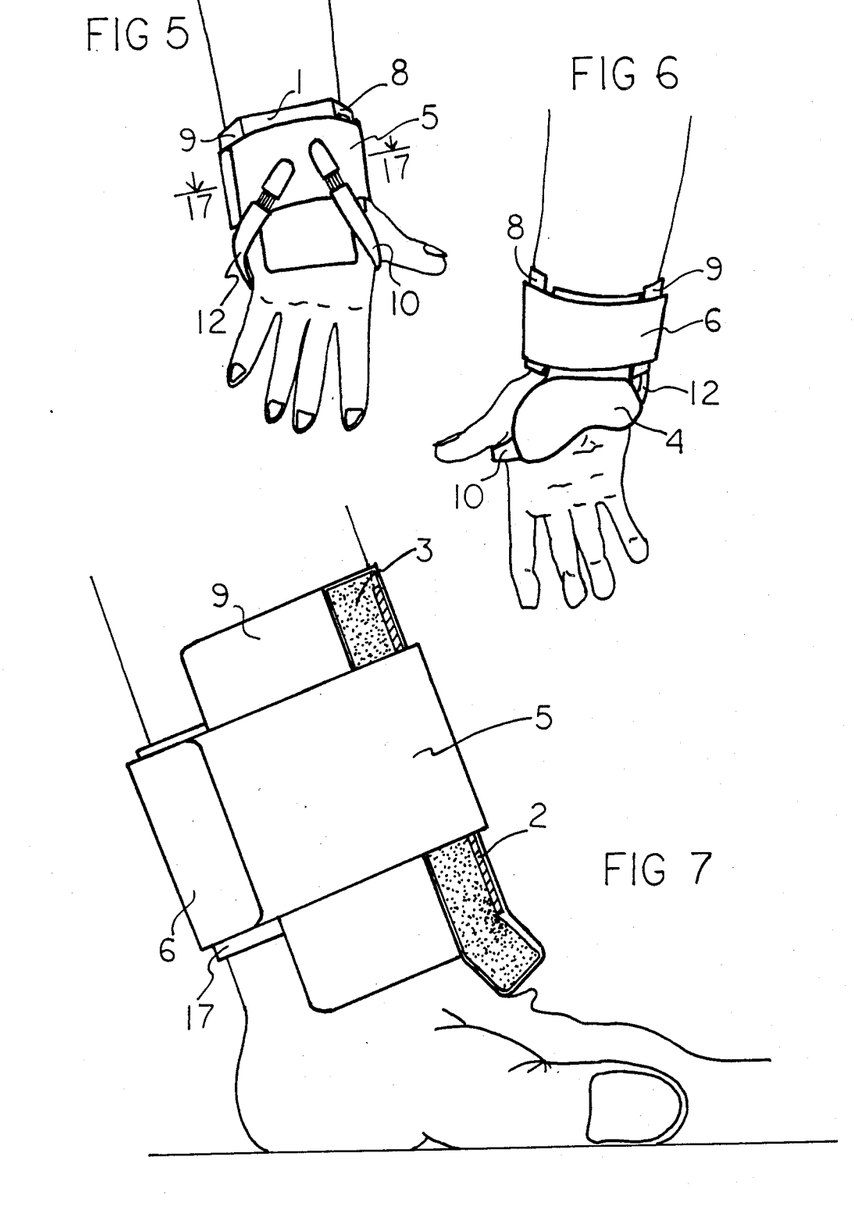
FIG. 5 shows a perspective view of the back side of the wrist brace as it contours the wrist and hand.
FIG. 6 shows a perspective view of the front side of the wrist brace as it contours the wrist and hand.
FIG. 7 shows a schematic side view of the wrist brace without the palmar pad in an extended support position.

Additionally, this wrist orthotic uses a more durable, stronger pad on the dorsal (back) side of the hand. In this dorsal pad, a member consisting of a more rigid material (preferably "Orthoplast") is adhered to the top of the malleable member, preferably consisting of trademark "Ethafoam", such that the Ethafoam pad will not bend as easily under pressure, thus creating a longer lasting dorsal pad. In the prior art wrist brace the Ethafoam pad is thin, making it necessary to be replaced quite frequently because it lacks this extra rigid member. The Orthoplast in the proposed brace is attached to the Ethafoam such that it remains equally as comfortable to the user while still providing a better and more rigid support than the prior art wrist brace in an extended support position. A drawing of the dorsal pad is shown in FIG. 7.

Another object and advantage in this invention, is the trademark "Velcro" attachment of the palmar variance pad to the wrist strap. The advantages of this feature are three-fold:

it allows each gymnast to position this pad according to personal comfort and/or effectiveness, it allows the individual to change the palmar variance pad according to his ulnar variance (drawn from a radiograph), and, it allows the user to disregard the palmar pad for exercises that might be more comfortable without it (e.g., uneven/parallel bars, high bar, pommel horse), without losing the support from the dorsal side of the brace. No prior art wrist brace shows such versatility in its use.

Further objects and advantages of this invention will become apparent from a consideration of the drawings and ensuing description thereof.

REFERENCE NUMERALS

1. Dorsal base support pad
2. Rigid support member
3. Malleable support member
4. Palmar variance pad
5. Loop Velcro wrist strap
6. Hook Velcro wrist strap
7. Rectangular ring
8. Left dorsal side pad
9. Right dorsal side pad
10. Long palmar strap
11. Hook Velcro long palmar strap
12. Short palmar strap
13. Hook Velcro short palmar strap
14. Elastic
15. Bottom fabric layer
16. Top fabric layer
17. Protection flap
18. Palmer hook Velcro patch
19. Alternative radial pad
20. Alternative ulnar pad
21. Radius
22. Ulna

DESCRIPTION OF THE PREFERRED EMBODIMENT

Figure 15:
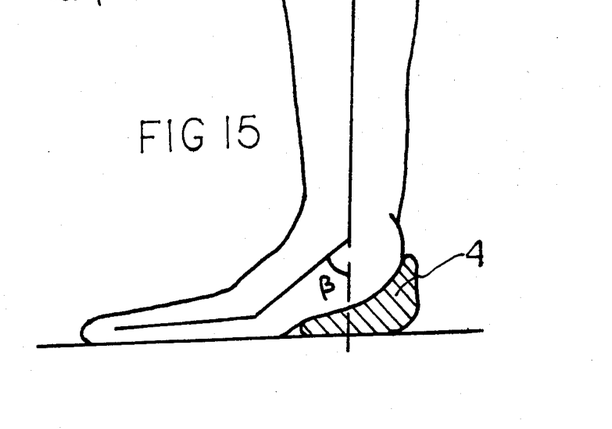
FIG. 15 shows a conceptual illustration of the extension angle β with the palmar pad.

FIGS. 1 thru 5 show this wrist support, consisting of two separable pieces; first the dorsal base support 1 attached to the Velcro wrist strap 5, and second, the palmar variance pad 4 (shown as a separate member in FIG. 15).

Figure 13:
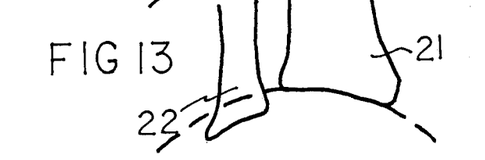
FIG. 13 shows a conceptual drawing of positive ulnar variance (a condition commonly seen in gymnasts).
Figure 16:
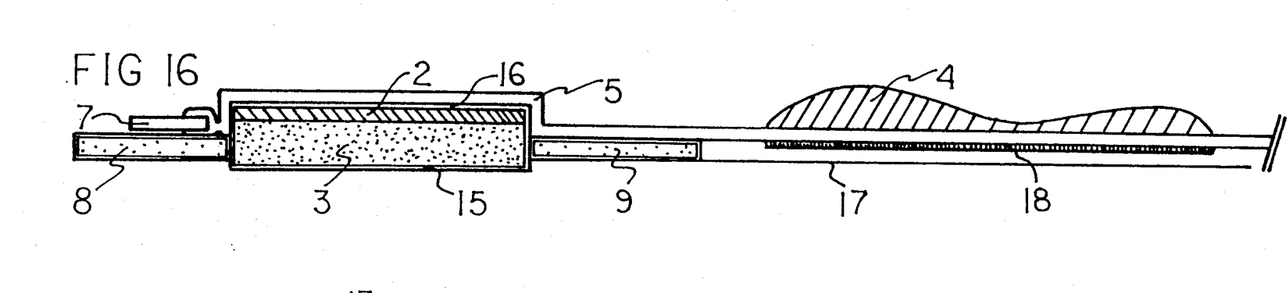
FIG. 16 shows a cross sectional view of the brace as seen in the direction of arrow 16 in FIG. 18, in a flattened position.

A plastic or metal rectangular ring 7, the size of the width of the Velcro wrist strap 5, is attached to the wrist strap's end. This Velcro wrist strap 5 is stitched on to the top layer of durable fabric 16, such as canvas, that surrounds the dorsal pad 1 and both dorsal side pads 8,9. The bottom fabric layer 15 is attached to the top fabric layer 16 by means of stitches along the outer edges of the dorsal pad 1 and left 8 and right 9 dorsal side pads. The two fabric layers 15, 16 are also stitched together between the dorsal side pad 1 and both side pads 8,9 as illustrated in FIG. 13. This divides the dorsal part of the wrist brace into three panels (one is large and two are smaller) into which the dorsal pad 1 and both side pads 8,9 fit. The side pads 8,9 are smaller than the central dorsal pad and are made out of preferrably a resilient material such as white closed cell foam. The central dorsal reinforcing member 1 consists of an elongated piece of malleable material 3, such as an Ethafoam pad, and an elongated piece of a rigid material 2, such as Orthoplast, which has the same width but shorter length and thickness. In FIG. 6 and 7, the reader can notice how the rigid support member 2 is attached on top of the malleable support member 3. These 2 and 3 are adhered (e.g. glued or taped) into one unit, such that the longer part of the malleable support member 3 sticks out on the distal side of the dorsal pad 1. Instead of Orthoplast, another material which is resilient and which gives very little under pressure, may be appropriate. Instead of using fabric layers 15, 16 it is preferable to select a tough, durable and longitudionally elastic fabric which does not irritate the skin and which absorbs the user's perspiration. Alternatively, one piece of a malleable support member 3 might be better than the fabric layers 15,16 with three different compartments 1,8,9. The general shape would remain the same but the dorsal pad 1 would somehow be integrated into this malleable dorsal support member 3, as is shown in the alternative invention in FIGS. 16,17.

Figure 1:
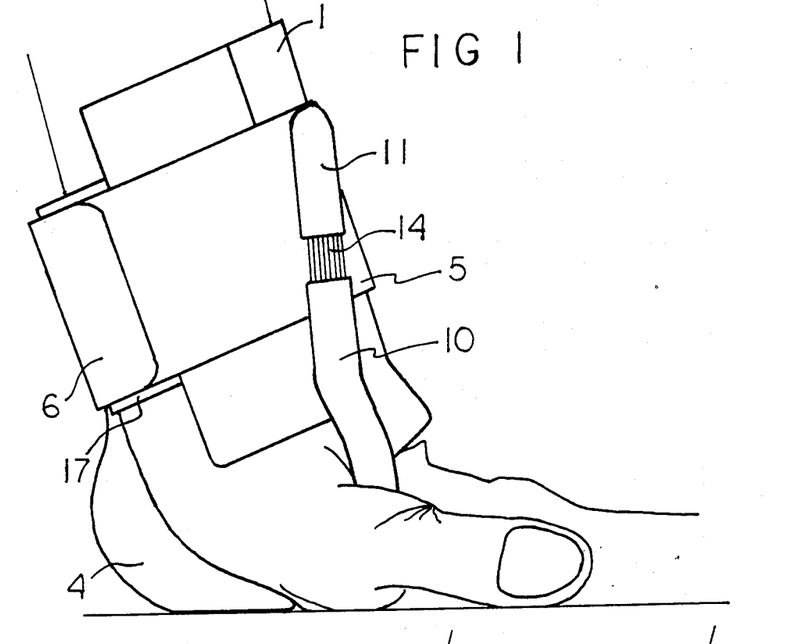
FIG. 1 shows a schematic side view of the thumb (radial) side of the wrist brace on the hand in an extended support position.
Figure 2:
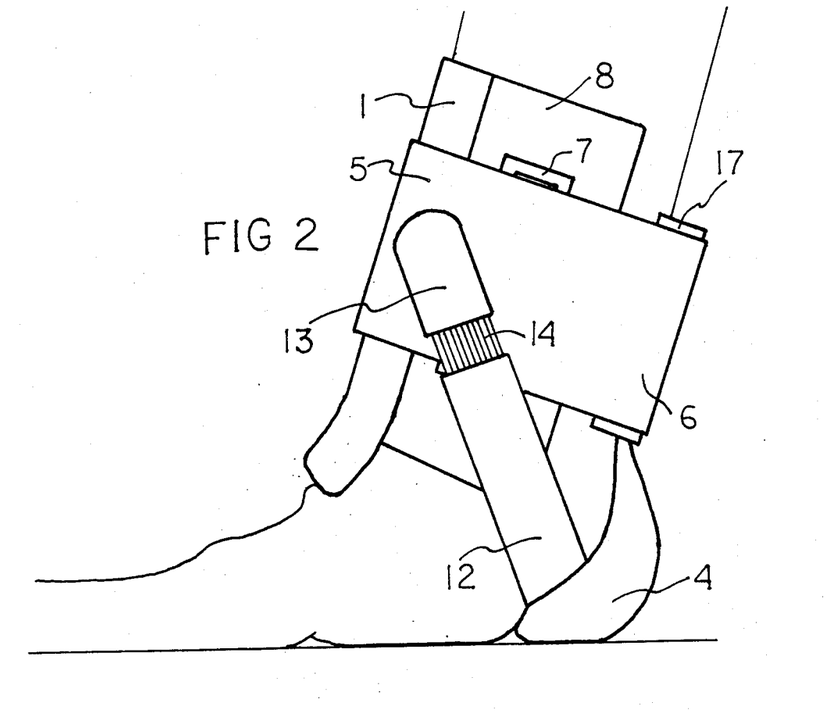
FIG. 2 shows a schematic side view of the little finger (ulnar) side of the wrist brace on the hand in an extended support position.
Figure 3:
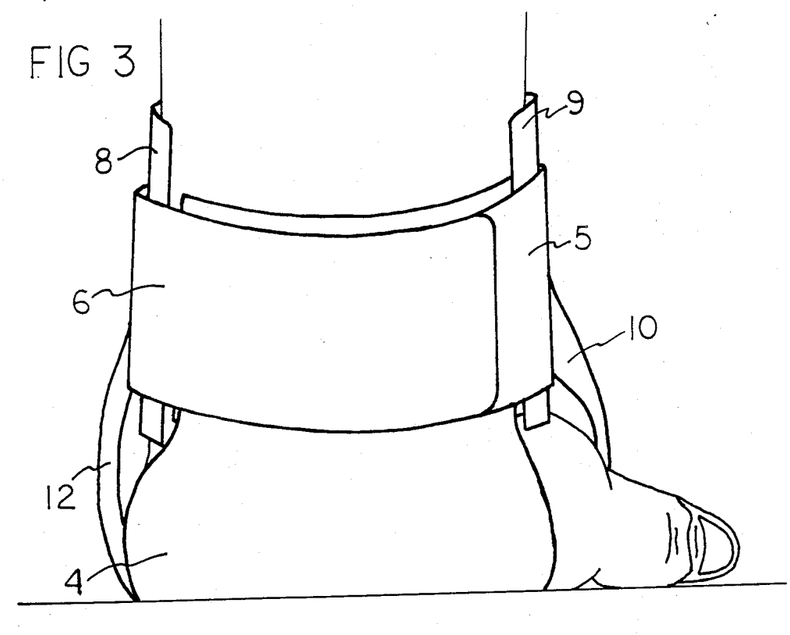
FIG. 3 shows a schematic front view of the wrist brace on the hand in an extended support position.
Figure 4:
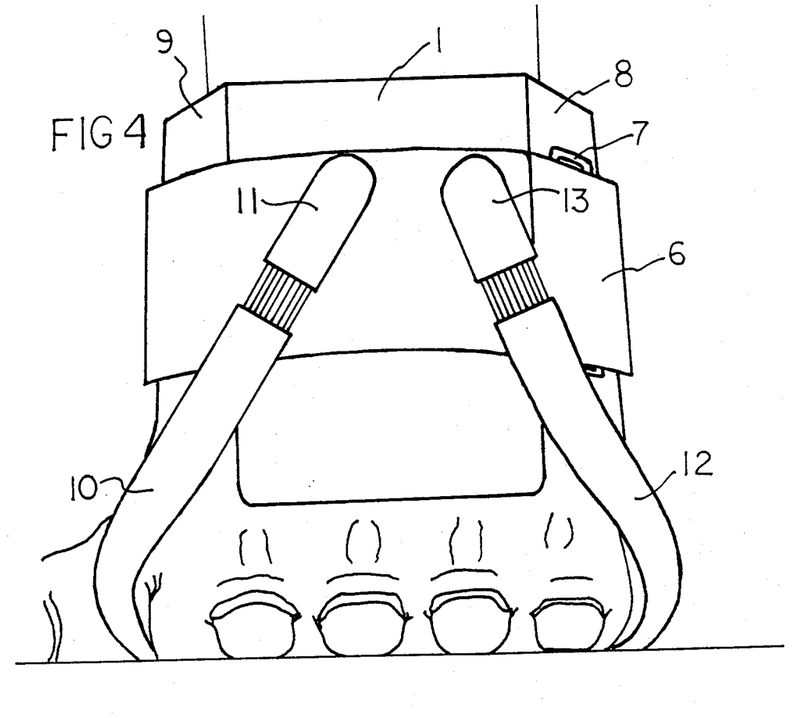
FIG. 4 shows a schematic back view of the wrist brace on the hand in an extended support position.

The loop Velcro wrist strap 5, which is stitched loop side down onto the top fabric layer 16, is approximately 40 cm. long. At its endpoint, the hook part of the Velcro wrist band 6 is attached (preferrably stitched) to the opposite face side of the loop Velcro wrist strap 5. This hook velcro wrist strap 6 is approximately 18 cm. long. The Velcro wrist strap 5,6 is approximately half the width of the dorsal base support 1. Approximate measurements can be taken from FIGS. 6 and 7, because these drawing are on a 1:1 scale. A protection flap 17 is stitched onto the edge of the right dorsal pad 9 and is positioned between the skin and the palmar pad 4, or wrist strap 5 when palmar pad 4 is detached, to reduce pressure on the user's skin. In FIG. 15, the reader can see how the palmar variance pad consists of a palmar pad 4 that fits between a top 16 and a bottom 15 durable fabric layer, such as canvas, with a long strap 10 and a short strap 12 attached (stitched) to the top side of the palmar pad 4. The long strap 10 consists of a top 16 and bottom 15 durable fabric strap, such as canvas, with a short elastic 14 and a short hook Velcro 13. This short hook Velcro 13 snaps on to the loop Velcro side of the wrist strap 5 after it is wrapped all the way around the wrist. The long strap 10 goes around the thumb as shown in FIGS. 1,3, and 4. The short strap 12 also has an elastic 14 and a hook Velcro end 13. This hook Velcro end 13 snaps also onto the loop Velcro wrist strap along the little finger side as shown in FIGS. 2,3, and 4.

The palmar base support as one member (4,10,11,12,13,14 and 18) is snapped onto the loop Velcro wrist strap 5 with the palmar hook Velcro 18. The palmar pad 4 is in the shape drawn in FIG. 13 and 15, and consists of preferably a compact nylon and cotton material, such as the material used in a trademark "Hapad" arch support. The exact thickness and angulation of this palmar pad 4 may be varied, depending on the personal ulnar variance, as shown in FIG. 8. Also the nature of the material used, might be changed after more research is done. The dotted line in FIG. 8, shows a more positive ulnar variant wrist, in which angle γ' is greater than γ (lesser positive variance), resulting in a higher radial side of the palmar pad, as compared to the ulnar side. More research is also needed to obtain ideal measurements of the palmar pad 4 for the average gymnast. In addition, the size of the palmar pad 4 can be customized according to the user's needs. The wrist brace can also be used without the palmar support base 4. Its appearance without 4, is shown in FIG. 6 and 14.

Figure 14:
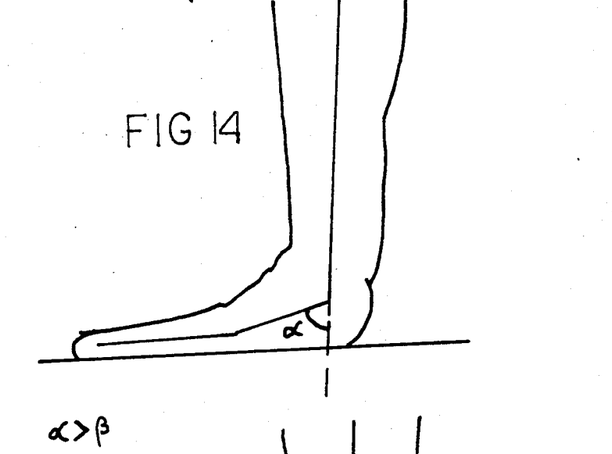
FIG. 14 shows a conceptual illustration of the extension angle α without the palmar 1.

The approximate measurements of the brace in FIGS. 13 and 14 are for a large size brace. The sizes of the brace will depend upon the hand size of the gymnast.

Figure 17:
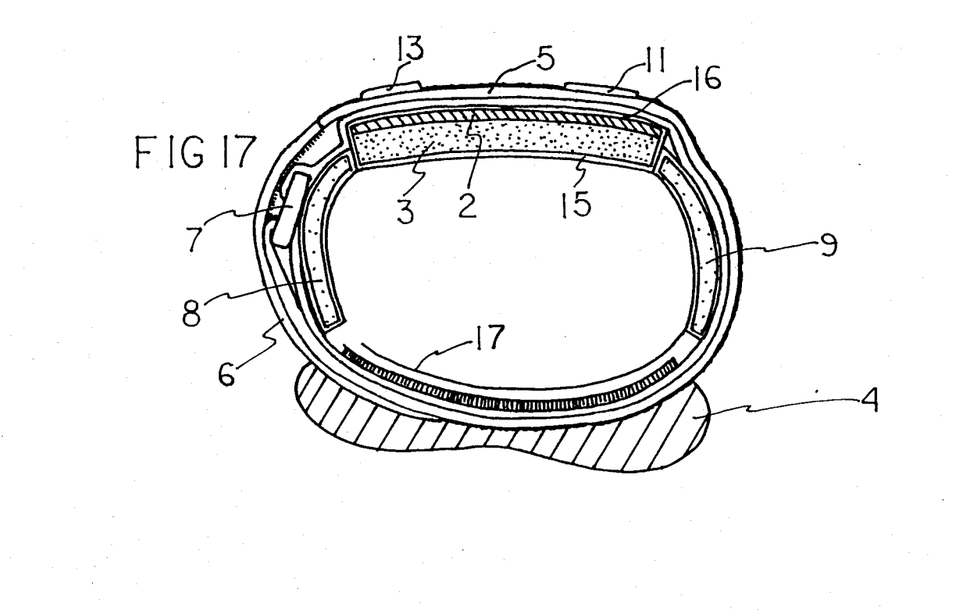
FIG. 17 shows a cross sectional view of the brace in FIG. 16 as it contours the wrist.
Figure 18:
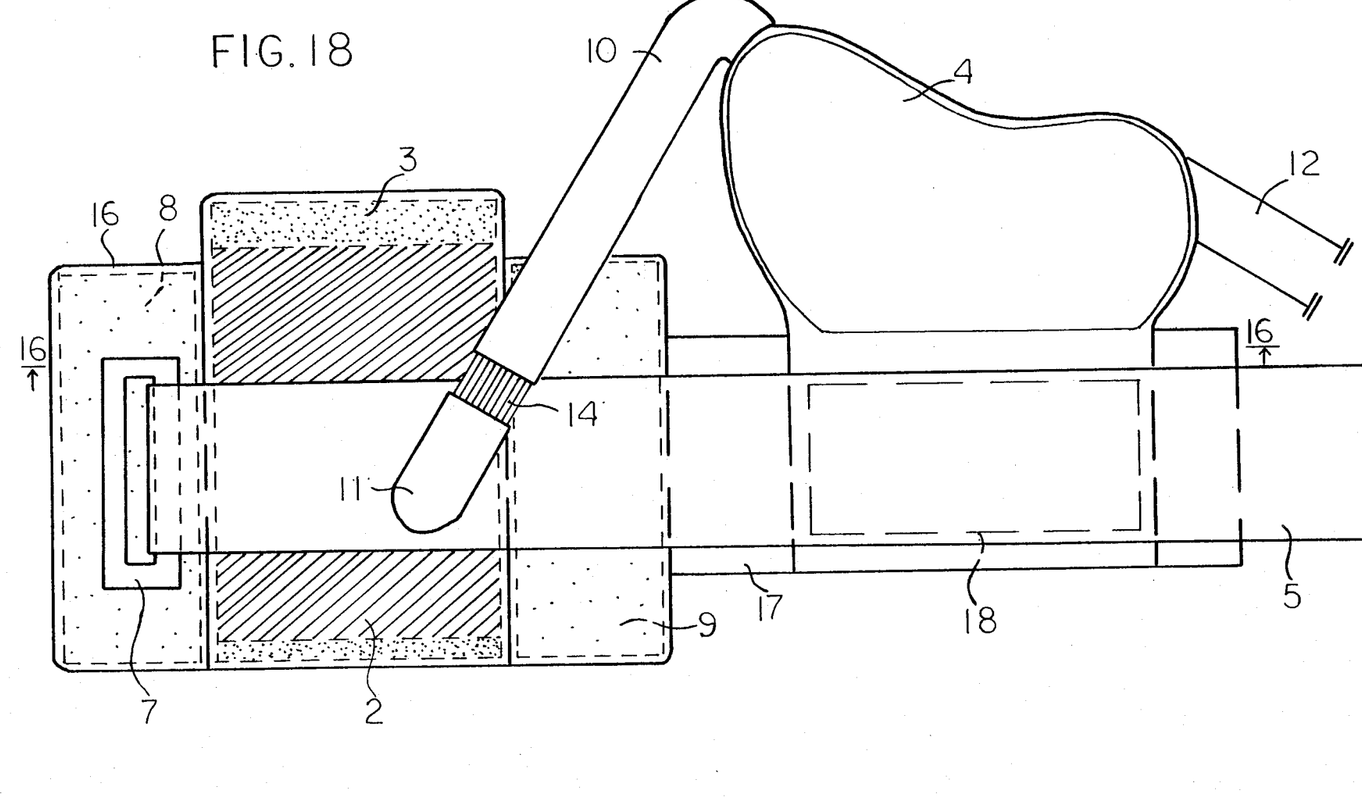
FIG. 18 shows a top view of the brace in a flattened position, including the palmar base support.
Figure 19:
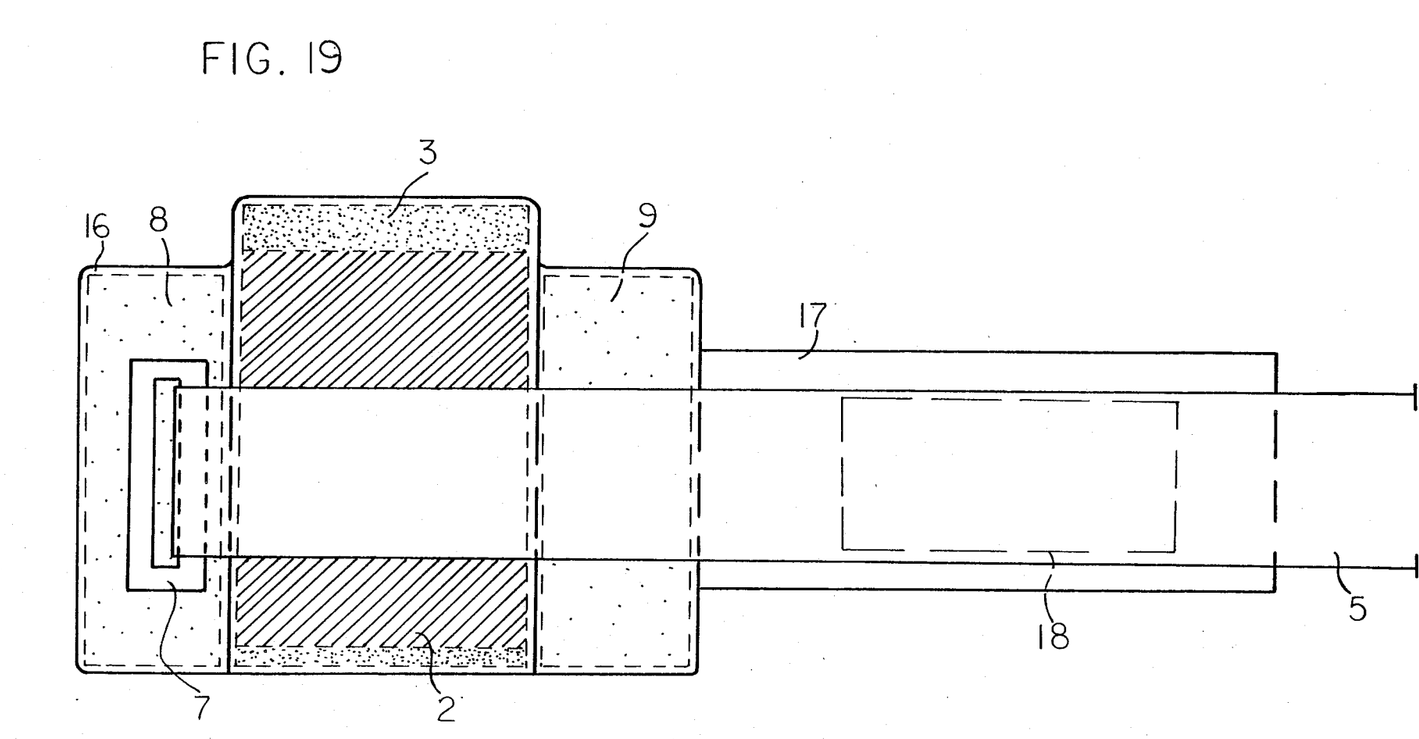
FIG. 19 shows a top view of the brace in a flattened position, excluding the palmar base support.
Figure 20:
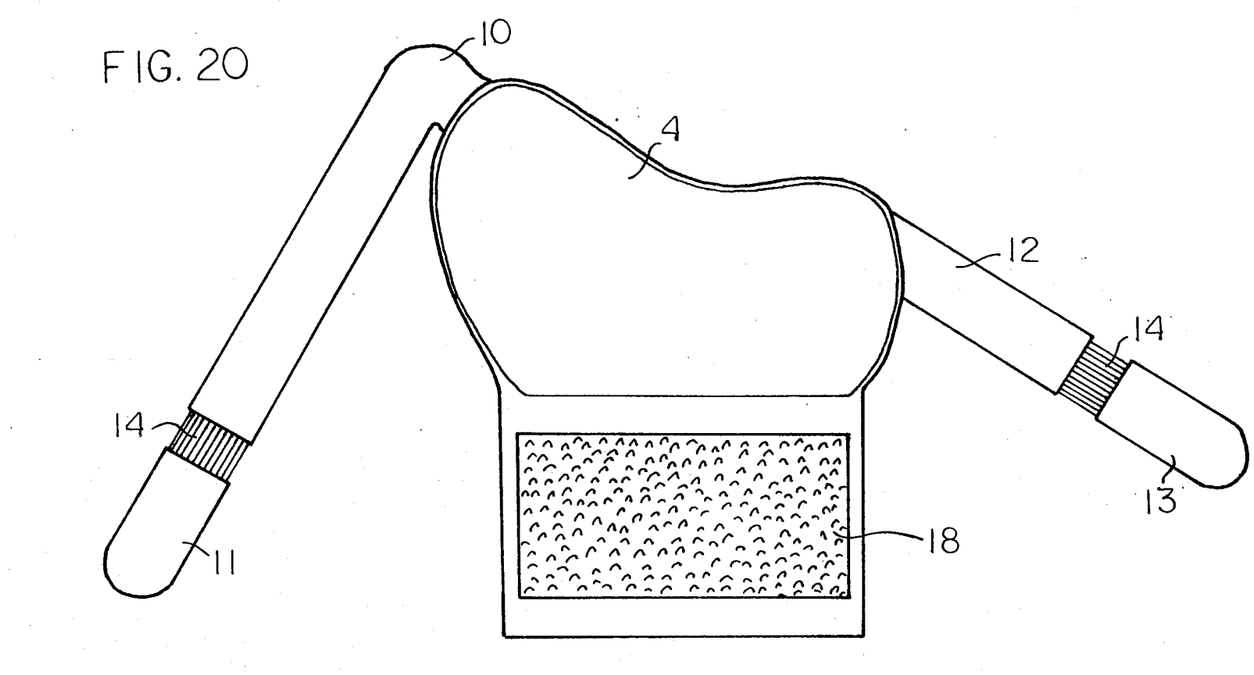
FIG. 20 shows a top view of the palmar variance pad as a separate member.
Figure 21:
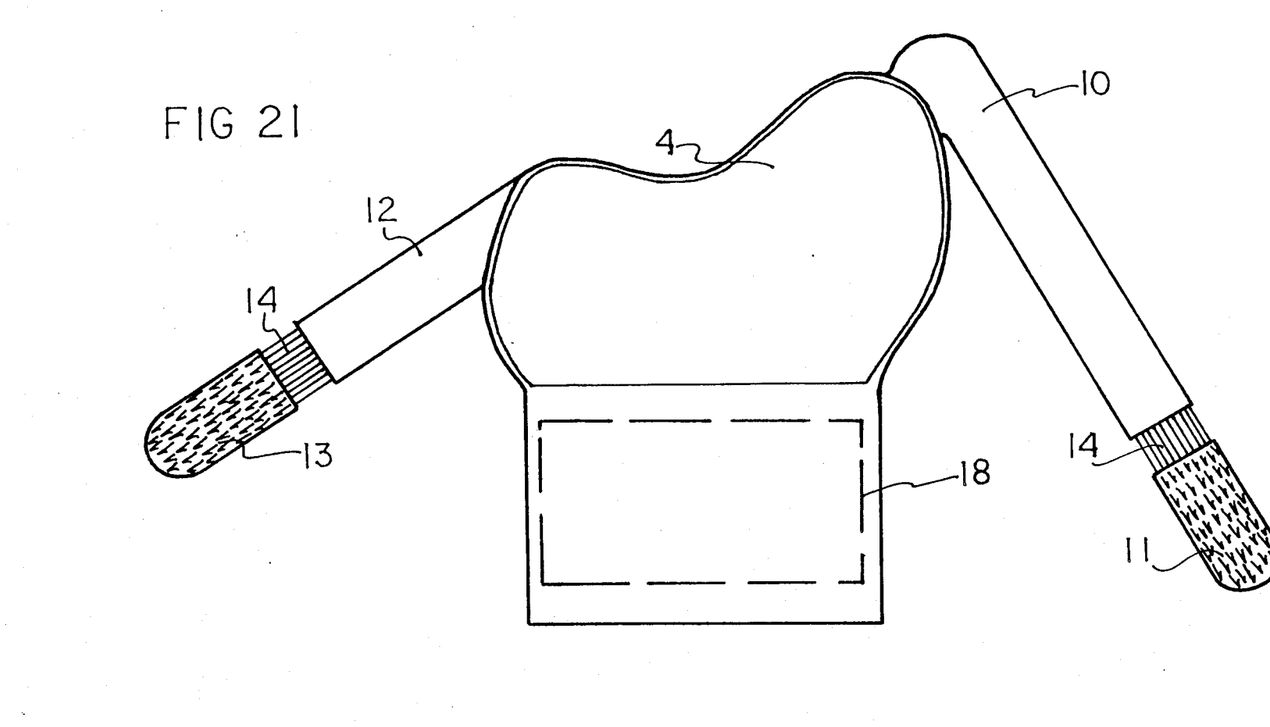
FIG. 21 shows a bottom view of the palmar variance pad as a separate member.
Figure 22:
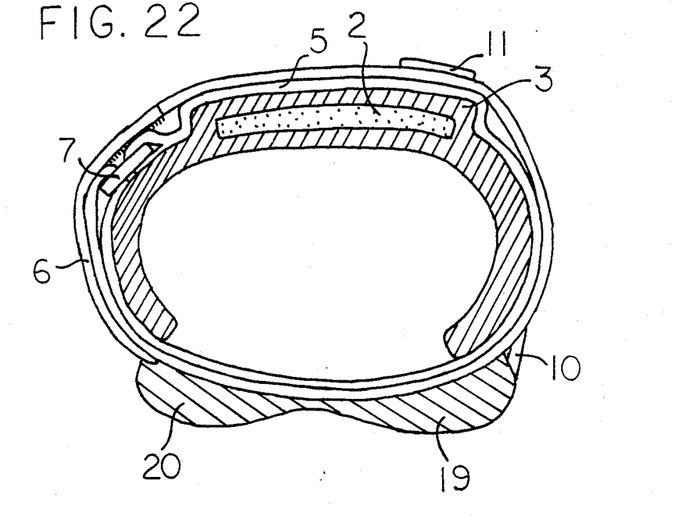
FIG. 22 shows a cross sectional view of an alternative brace as it contours the wrist, as seen in the direction of the arrow 24 in FIG. 23.
Figure 23:
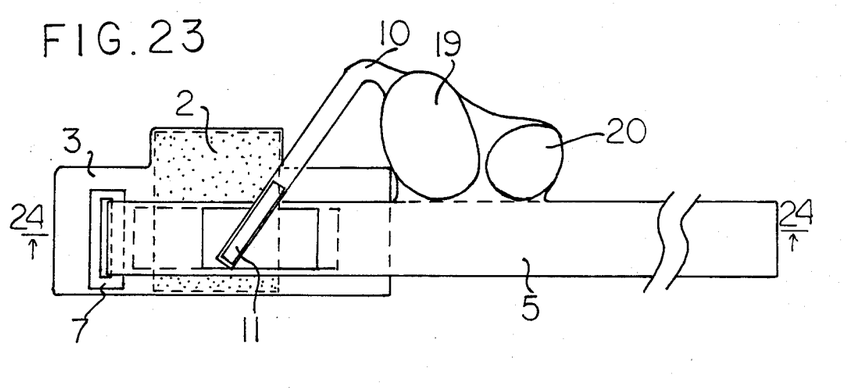
FIG. 23 shows a stop view of the alternative wrist brace in FIG. 22 in a flattened position.
Figure 24:
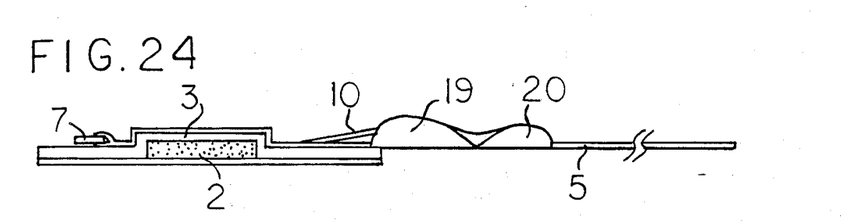
FIG. 24 shows a cross sectional view of the alternative wrist brace in FIG. 22 in a flattened position.

Two separate pads 19,20 as shown in FIG. 17, could be an alternative design, although this might produce less favorable results. Different materials might be used if proven more effective without changing the basic claims of this invention.

OPERATION OF INVENTION

Figure 10:
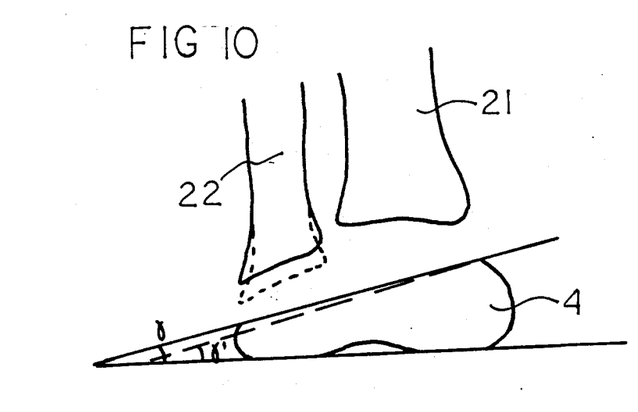
FIG. 10 shows a conceptual illustration of how the palmar pad compensates for different degrees of ulnar variance.
Figure 11:
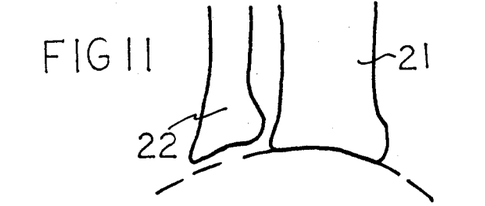
FIG. 11 shows a conceptual drawing of negative ulanar variance.
Figure 12:
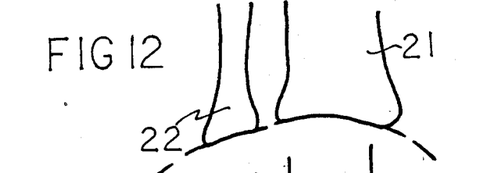
FIG. 12 shows a conceptual drawing of neutral ulnar variance.

This invention performs a wide variety of specific supports of the wrist joint. As an Olympic gymnast myself, I am very familiar with the problems that gymnasts face every day. Many wrist injuries occur as the result of chronic overuse of the wrist bones, tendons, and cartilage in the excessive weight bearing supports on the apparatus and the floor exercise. Although many prior art braces have been made to support the wrist joint, none have been designed to reduce the painful extension angle in a support position. Only with the use of this invention's palmar variance pad 4, the angle α will be reduced to angle β as shown in FIG. 10. This new design allows the gymnast to increase his training intensity (because less pain) and ultimately perform better as a gymnast. Many competitive gymnasts lose a lot of valuable training hours due to wrist pain. This invention allows the user to continue workouts at a lower pain level. As the captain of the UCLA gymnastics team (NCAA Champions in 1987) I had the privilege to have some of my teammates experience this invention. Not only was everyone enthusiastic because the wrist orthotic relieved the pressure of their sore wrists, but it also biomechanically facilitated certain gymnastic skills such as front hand spring, back hand springs, walk overs, flair circles on floor, and many other skills.

The Velcro straps 5,6,11,13 make application of this wrist brace very easy and fast. It only takes five seconds to wrap and position this brace around the user's wrist. The Velcro wrist strap 5,6 also makes the brace adjustable according to the size and circumference of the wrist.

The dorsal pad 1 and its side members 8,9 are positioned on the back side of the wrist and covering the lower part of the hand. FIGS. 11 thru 14 show how the dorsal pad 1 is connected to a Velcro wrist strap 5 which wraps around the wrist. A variance palmar pad 4 is held into place by the Velcro wrist strap 5 which snaps onto the palmar hook Velcro patch 18. The Velcro wrist strap 5 fits through the rectangular ring and is pulled towards the opposite direction by the user. Reversing direction of the Velcro wrist strap 5 thru the rectangular ring 7 positioned the brace in a snug position around the wrist. Finally the hook side of the Velcro wrist strap 6 is adhered to the loop side of the same wrist strap 5 which is already positioned around the user's wrist, to secure the brace's position.

The palmar variance pad 4 is positioned such that the thicker, larger part is on the thumb (radial) side. The smaller, thinner part is to be fitted a little lower on the little finger (ulna) side. FIG. 5 (I and II) shows this position to the reader. Once the variance palmar pad 4 is positioned right, the user pulls the long 10 and short 12 strap and adheres them to the hook Velcro 11,13 onto their respective positions on the loop Velcro side of the wrist strap 5 in a position shown in FIG. 4. The elastic 14 allows for tightness preference and for greater mobility in flexion of the hand as needed. Most prior art wrist braces do not allow the same amount of flexion and are more restrictive in this motion. The gymnast however, prefers to be able to flex his hand without restriction.

In circumstances where the palmar variance pad 4 might be disturbing, such as on parallel/uneven bars, the user can disregard the palmar hook Velcro patch 18 off the wrist strap 5. The protection patch 17 is then positioned between the skin and the wrist strap loop Velcro 5 in order to prevent cutting into the user's skin. The palmar variance pad 4 is shown in FIG. 15 after it is separated from the wrist strap 5. The brace is still very useful without its palmar pad 4, as shown in FIG. 6, and can be used in a variety of sports where wrist stability is needed. No such versatility is present prior art wrist braces.

Besides the fact that the palmar pad 4 elevates the wrist as one segment (reducing the extension angle), the thicker thumb side part (radius) of the palmar pad 4 is based on results from the scientific study I engaged in with the UCLA Orthopedic Sports Medicine Group. As collaborator of the paper entitled "The Gymnast's Wrist Pain Syndrome", I won an award in the category "Young Investigator" by the American Orthopedic Society of Sports Medicine in 1987. Our findings indicated a high incidents of positive ulnar variance (see FIG. 9 (III)) in gymnasts, indicating that the ulna is longer relative to the radius. This might be the result of premature closure of the growth plate in the radius, as a consequence of continuous loading of the radius (this bone takes 60% of all axial loads in the forearm) in adolescent gymnasts. The shape of the palmar variance pad 4 in this invention does the following: it corrects/compensates imbalanced forces in the wrist joint caused by positive or negative ulnar variance, and it prevents bone growth deformities in the maturing gymnast by cushioning the radius and ulna.

Thus the reader will realize that this invention could bring a radical change in the prevention and/or correction of wrist problems in excessive weight bearing activities, such a gymnastics.

While the above description contains many specificities, these should not be construed as limitations on the scope of the invention, but rather as an exemplification of one preferred embodiment thereof. Many variations are possible. For example, a company specializing in orthotics can reduce the brace's bulkiness using different, lighter materials without changing the scope and effectiveness of this invention. The ideal height and angulation of the palmar variance pad 4 must be calculated according to findings from future tests using an electrodynagram which assesses the force distribution on the hand in a support position. Similar to arches for a pronated foot, the best shape for the palmar pad 4 will be found to compensate for the individual's ulnar variance. Changing the palmar variance pad 4 according to individual ulnar variance differences (as examined on a radiograph), is facilitated by the snap on feature of the hook Velcro patch 18 onto the loop Velcro wrist strap 5.

This invention is not limited to gymnasts or athletes, but finds its application in any activities requiring wrist stability, especially in an extended position. Accordingly, the scope of this invention should be determined not by the embodiment, but by the appended claims and their legal equivalents.

I claim:

1. A wrist supporting device for gymnasts comprising, in combination, a dorsal body of flexible sheet material positioned to contour the back of the user's wrist and lower one third of said user's metacarpal bones,
    said dorsal body having three pockets whereof two lateral pockets are positioned on each side of said user's wrist, each containing a pad of resilient material,
    said dorsal body having a central pocket, enclosing a thick malleable support member of said resilient material, reinforced by a more rigid support member positioned on the free surface of said malleable support member and said rigid support member having a longitudinal dimension shorter on the distal end than said malleable support member,
    said central pocket covering substantially the width of said user's wrist and said lower third of said metacarpals and being elongated more towards distal margin than said lateral pockets when said dorsal body is wrapped around said user's wrist, and means for wrapping said dorsal body around said wrist whereby a wrist strap is secured to said dorsal body, encircling said wrist, then looping through a ring attached to the beginning of said wriststrap, tightly pulled in reverse direction by said user to secure a loose end to removably adhering material on said beginning of said wriststrap, and a palmar body of said flexible sheet material which is sized and shaped to cover the front side of both said wrist and lower half of palm below proximal creaseline, thus covering said thumbside of said palm more distally than the covering of said little finger side of said palm, attachment means of said palmar body attaching said wriststrap on front of said wrist and using a long palmar strap emerging from said free edge of said thumbside wrapping around said thumb adhering to backside of said wriststrap, a short palmar strap emerging from distal end on said little finger side of said palmar body, wrapping around side of said hand adhering to backside of said wriststrap, and a palmer pad of said resilient material encased in said palmar body covering and cushioning lower portion of said palm, wherein upper edge of said palmer pad coincides with upper edge of said palmar body, and lower edge of said palmar pad extends only as far as the lower edge of said palm.

2. The device defined by claim 1 wherein said rigid support member of said resilient material such as polyethylene or copolymer, providing support to said thick malleable support member under high bending forces while allowing some elasticity of said rigid support member to provide comfort in said bending position at the wrist joint.

3. The device as defined in claim 2 wherein said thickness of said palmar pad on said radial side approximates one third inch as opposed to said ulnar side which approximates one fourth inch, resulting in a slope of said surface wherein said palmar pad is removable and adjustable to said user's specific ulnar variance measurements.

4. The device defined by claim 1 wherein said fastening means of said dorsal body includes a combination of a napped fabric wriststrap which loops through said ring and is continuous with a hook fabric wriststrap upon which it adheres.

5. The device defined by claim 1 wherein proximal part of said palmer body is sandwiched between said wriststrap and said user's wrist, adhered by cooperating fastening means to said wriststrap, enabling said user to remove said palmar body with said palmar pad when said palm needs full exposure.

6. The device defined by claim 1 wherein said palmar pad has increased thickness on said thumbside leveling its surface downward to said little finger side and peripherally towards the edges, as a measure to restore imbalance between ulna and radius bone length.

7. The device defined by claim 1 whereby elastic material attaches said long palmar strap to a nylon type strip of material which removably adheres to another strip of nylon material on said wriststrap securing positioning of said palmar body.

8. The device defined by claim 1 whereby said elastic material attaches said long palmar strap to a said nylon type strip of material which removably adheres to said strip of nylon material on said wriststrap curing positioning of said palmar body.

* * * * *